United States Patent
Chan et al.

[11] Patent Number: 5,948,811
[45] Date of Patent: Sep. 7, 1999

[54] PHARMACEUTICAL COMPOSITION CONTAINING BICYCLIC TYPE COMPOUNDS

[75] Inventors: Wai Ngor Chan, Epping; John Morris Evans, Roydon; Geoffrey Stemp, Bishop's Stortford; Neil Upton, Harlow, all of United Kingdom; Robert Nicholas Willette, Pottstown, Pa.

[73] Assignee: SmithKline Beegham p.l.c., Brentford, Middlesex, United Kingdom

[21] Appl. No.: 08/852,890

[22] Filed: May 8, 1997

Related U.S. Application Data

[63] Continuation of application No. 08/448,519, filed as application No. PCT/GB93/02513, Dec. 8, 1993, abandoned.

[30] Foreign Application Priority Data

Dec. 11, 1991 [GB] United Kingdom ............ 9225858
Dec. 11, 1992 [GB] United Kingdom ............ 9225857
Dec. 11, 1992 [GB] United Kingdom ............ 9225861

[51] Int. Cl.$^6$ .......... A61K 31/35; A61K 31/38; C07D 409/12; C07D 311/68
[52] U.S. Cl. .......... 514/444; 514/456; 549/60; 549/399
[58] Field of Search ............ 549/399, 60; 514/456, 514/444

[56] References Cited

U.S. PATENT DOCUMENTS 4,571,406  2/1986  Evans et al. ............ 514/456

FOREIGN PATENT DOCUMENTS 0 139 992 A1  8/1984  European Pat. Off. .
0 271 271 A2  11/1987  European Pat. Off. .
WO 92/22293  12/1992  WIPO .

OTHER PUBLICATIONS

Burrell, et al., Tetrahedron Letters; vol. 31, No. 25, pp. 3649–3652, (1990).
Ashwood, et al., J. Med. Chem; vol. 33, pp. 2667–2672, (1990).
Ashwood, et al. J. Med. Chem; vol. 34, pp. 3261–3267, (1991).

*Primary Examiner*—Laura L. Stockton
*Attorney, Agent, or Firm*—Mary E. McCarthy; Stephen Venetianer; Charles M. King

[57] ABSTRACT

A compound of formula (I) or pharmaceutically acceptable salt thereof:

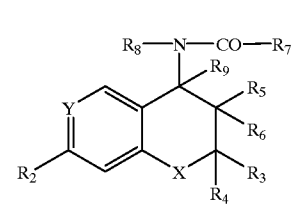

(I)

wherein either Y is N and $R_2$ is hydrogen, or Y is C—$R_1$; where either one of $R_1$ and $R_2$ is hydrogen and the other is selected from the class of hydrogen, $C_{3-8}$ cycloalkyl, $C_{1-6}$ alkyl optionally interrupted by oxygen or substituted by hydroxy, $C_{1-6}$ alkoxy or substituted arminocarbonyl, $C_{1-6}$ alkylcarbonyl, $C_{1-6}$ alkoxycarbonyl, $C_{1-6}$ alkylcarbonyloxy, $C_{1-6}$ alkoxy, nitro, cyano, halo, trifluoromethyl, $CF_3S$, or a group $CF_3$—A—, or a group $CF_2H$—A'—, trifluoromethoxy, $C_{1-6}$ alkylsulphinyl, perfluoro $C_{2-6}$ alkylsulphonyl, $C_{1-6}$ alkylsulphonyl, $C_{1-6}$ alkoxysulphinyl, $C_{1-6}$ alkoxysulphonyl, aryl, heteroaryl, arylcarbonyl, heteroarylcarbonyl, phosphono, arylcarbonyloxy, heteroarylcarbonyloxy, arylsulphinyl, heteroarylsulphinyl, arylsulphonyl, heteroarylsulphonyl, $C_{1-6}$ alkylcarbonylamino, $C_{1-6}$ alkoxycarbonylamino, $C_{1-6}$ alkylthiocarbonyl, $C_{1-6}$ alkoxy-thiocarbonyl, $C_{1-6}$ alkylthiocarbonyloxy, 1-mercapto $C_{2-7}$ alkyl, formyl, or aminosulphinyl, aminosulphonyl or aminocarbonyl, or $C_{1-6}$ alkylsulphinylamino, $C_{1-6}$ alkylsulphonylamino, $C_{1-6}$ alkoxysulphinylamino or $C_{1-6}$ alkoxysulphonylamino, or ethylenyl terminally substituted by $C_{1-6}$ alkylcarbonyl, nitro or cyano, or —$C(C_{1-6}$ alkyl)NOH or —$C(C_{1-6}$ alkyl)NNH$_2$, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl; or $R_1$ and $R_2$ together are —$(CH_2)_4$— or —CH=CH—CH=CH—, or form an optionally substituted triazole or oxadiazole ring; $R_3$ to $R_9$ represent various substituent groups; and X is oxygen or $NR_{10}$ where $R_{10}$ is hydrogen or $C_{1-6}$ alkyl.

9 Claims, No Drawings

PHARMACEUTICAL COMPOSITION CONTAINING BICYCLIC TYPE COMPOUNDS

This is a continuation of application Ser. No. 08/448,519, filed Jul. 7, 1995 now abandoned, which is a 371 of PCT/GB93/02513 filed Dec. 8, 1993.

This invention relates to novel compounds, to processes for preparing them, and to their use as therapeutic agents.

European Published Patent Application No. 0126311 discloses substituted benzopyran compounds having blood pressure lowering activity, including 6-acetyl-trans-4-(4-fluorobenzoylamino)-3,4-dihydro2,2-dimethyl-2H-1-benzopyran-3-ol.

Also EP-A-0 376 524, EP-A-0 205 292, EP-A-0 250 077, EP-A-0 093 535, EP-A-0 150 202, EP-A-0 076 075 and WO/89/05808 (Beecham Group plc) describe certain benzopyran derivatives which possess anti-hypertensive activity.

EP-A-0 350 805 (Biersdorf), EP-A-0 277 611, EP-A-0 277612, EP-A-0 337 179 and EP-A-0 355 565 (Hoechst Aktiengesellschaft); EP-A-0 466 131 (Nissan Chemical Industries Ltd), EP-A-0339562 (Yoshitomi Pharmaceuticals) EP-A-415 065 (E. Merck) EP-A-450415 (Squibb), EP-A-0482934, EP-A-0296975, JO-2004-791 and WO\89\07103 also describe certain benzopyran derivatives which are believed to possess anti-hypertensive activity.

EP-A-0 430 621 and EP-A-0 385 584 (Beecham Group plc) describe the resolution of certain intermediates useful in the preparation of the compounds described in the above mentioned patent applications.

EP-A-0 139 992 (Beecham Group plc) describes certain benzopyran derivatives which have cis isomerism at position 3 and 4 which compounds are described as possessing anti-hypertensive activity.

PCT/GB92/01045 (SmithKline Beecham plc; unpublished at the priority date), which describes certain fluorobenzoylamino benzopyrans, pyranopyridines and tetrahydronaphthalenes in which the 3 and 4 position substituents are trans to each other. These compounds are described as possessing inter alia anxiolytic and anti-convulsant activity.

It has now been surprisingly found that certain compounds of formula (I) (below) possess anti-convulsant activity, and are also believed to have utility in the treatment or prevention of anxiety, mania, depression, disorders associated with a subarachnoid haemorrhage or neural shock, the effects associated with withdrawal from substances of abuse, Parkinson's Disease, Psychosis, migraine and/or cerebral ischaemia.

Accordingly, the present invention provides a compound of formula (I) or pharmaceutically acceptable salt thereof:

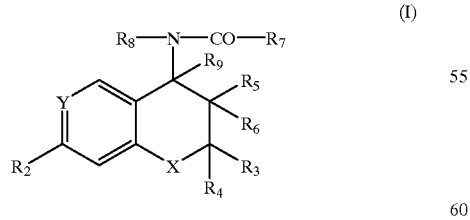

(I)

wherein:
either Y is N and $R_2$ is hydrogen, or Y is C—$R_1$
where:
either one of $R_1$ and $R_2$ is hydrogen and the other is selected from the class of hydrogen, $C_{3-8}$ cycloalkyl, $C_{1-6}$ alkyl optionally interrupted by oxygen or substituted by hydroxy, $C_{1-6}$ alkoxy or substituted aminocarbonyl, $C_{1-6}$ alkylcarbonyl, $C_{1-6}$ alkoxycarbonyl, $C_{1-6}$ alkylcarbonyloxy, $C_{1-6}$ alkoxy, nitro, cyano, halo, trifluoromethyl, $CF_3S$, or a group $CF_3$—A—, where A is —$CF_2$—, —CO—, —$CH_2$—, CH(OH), $SO_2$, SO, $CH_2$—O, or CONH, or a group $CF_2H$—A'— where A' is oxygen, sulphur, SO, $SO_2$, $CF_2$ or CFH; trifluoromethoxy, $C_{1-6}$ alkylsulphinyl, perfluoro $C_{2-6}$ alkylsulphonyl, $C_{1-6}$ alkylsulphonyl, $C_{1-6}$ alkoxysulphinyl, $C_{1-6}$ alkoxysulphonyl, aryl, heteroaryl, arylcarbonyl, heteroarylcarbonyl, phosphono, arylcarbonyloxy, heteroarylcarbonyloxy, arylsulphinyl, heteroarylsulphinyl, arylsulphonyl, heteroarylsulphonyl in which any aromatic moiety is optionally substituted, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl, formyl, or aminosulphinyl, aminosulphonyl or aminocarbonyl, any amino moiety being optionally substituted by one or two $C_{1-6}$ alkyl groups, or $C_{1-6}$ alkylsulphinylamino, $C_{1-6}$ alkylsulphonylamino, $C_{1-6}$ alkoxysulphinylamino or $C_{1-6}$ alkoxysulphonylamino, or ethylenyl terminally substituted by $C_{1-6}$ alkylcarbonyl, nitro or cyano, or —C($C_{1-6}$ alkyl)NOH or —C($C_{1-6}$ alkyl)NNH$_2$, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl; or $R_1$ and $R_2$ together are —$(CH_2)_4$— or —CH=CH—CH=CH—, or form an optionally substituted triazole or oxadiazole ring;

one of $R_3$ and $R_4$ is hydrogen or $C_{1-4}$ alkyl and the other is $C_{1-4}$ alkyl, $CF_3$ or $CH_2$ $X^a$ where $X^a$ is fluoro, chloro, bromo, iodo, $C_{1-4}$ alkoxy, hydroxy, $C_{1-4}$ alkylcarbonyloxy, —S—$C_{1-4}$ alkyl, nitro, amino optionally substituted by one or two $C_{1-4}$ alkyl groups; cyano or $C_{1-4}$ alkoxycarbonyl or $R_3$ and $R_4$ together are $C_{2-5}$ polymethylene optionally substituted by $C_{1-4}$ alkyl; $R_5$ is $C_{1-6}$ alkylcarbonyloxy, benzoyloxy, $ONO_2$, benzyloxy, phenyloxy or $C_{1-6}$ alkoxy and $R_6$ and $R_9$ are hydrogen or $R_5$ is hydroxy and $R_6$ is hydrogen or $C_{1-2}$ alkyl and $R_9$ is hydrogen;

$R_7$ is heteroaryl or phenyl; both of which are optionally substituted one or more times independently with a group or atom selected from chloro, fluoro, bromo, iodo, nitro, amino optionally substituted once or twice by $C_{1-4}$ alkyl, cyano, azido, $C_{1-4}$ alkyl, $C_{1-4}$ alkoxy, trifluoromethoxy and trifluoromethyl;

$R_8$ is hydrogen; $C_{1-6}$ alkyl, $OR_9$ or $NHCOR_{10}$ wherein $R_9$ is hydrogen, $C_{1-6}$ alkyl, formyl, $C_{1-6}$ alkanoyl, aroyl or aryl-$C_{1-6}$ alkyl and $R_{10}$ is hydrogen, $C_{1-6}$ alkyl, $C_{1-6}$ alkoxy, mono or di $C_{1-6}$ alkyl amino, amino, amino-$C_{1-6}$ alkyl, hydroxy—$C_{1-6}$ alkyl, halo-$C_{1-6}$ alkyl, $C_{1-6}$ acyloxy-$C_{1-6}$ alkyl, $C_{1-6}$ alkoxycarbonyl-$C_{1-6}$-alkyl, aryl or heteroaryl;

the $R_8$—N—CO—$R_7$ group being cis to the $R_5$ group; and X is oxygen or $NR_{10}$ where $R_{10}$ is hydrogen or $C_{1-6}$ alkyl with the proviso that the compound is not racemic cis-4-benzoylamino-6-cyano-3,4-dihydro-2, 2-dimethyl-2H-benzo[b]pyran-3-ol.

All $C_{1-6}$ alkyl or $C_{1-4}$ alkyl or alkyl containing groups in formula (I) are preferably selected from methyl, ethyl, n- and iso-propyl, n-, iso-, sec- and tert-butyl.

Suitable $C_{3-8}$ cycloalkyl groups include cyclopropyl, cyclobutyl, cyclopentyl, cyclohexyl, cycloheptyl and cyclooctyl.

Suitable halo substituents include fluoro, chloro and bromo.

Aryl whenever mentioned herein includes but is not limited to phenyl and naphthyl.

Heteroaryl whenever mentioned herein includes a 5- or 6-membered monocyclic or 9- or 10-membered bicyclic of which 5- or 6-membered monocyclic heteroaryl is preferred. In addition, 5- or 6-membered monocyclic or 9- or 10-membered bicyclic heteroaryl preferably contains one, two or three heteroatoms which are selected from the class of oxygen, nitrogen and sulphur and which, in the case of there being more than one heteroatom, are the same or different. Examples of 5- or 6-membered monocyclic heteroaryl containing one, two or three heteroatoms which are selected from the class of oxygen, nitrogen and sulphur include furyl, thienyl, pyrryl, oxazolyl, thiazolyl imidazolyl and thiadiazolyl, and pyridyl, pyridazyl, pyrimidyl, pyrazolyl and triazolyl. Preferred examples of such groups include furanyl, thienyl, pyrryl and pyridyl, in particular 2- and 3-furyl, 2- and 3-pyrryl, 2- and 3-thienyl, and 2-, 3- and 4-pyridyl. Examples of 9- or 10-membered bicyclic heteroaryl containing one, two or three heteroatoms which are selected from the class of oxygen, nitrogen and sulphur include benzofuranyl, benzothienyl, indolyl and indazolyl, quinolyl and isoquinolyl, and quinazolyl. Preferred examples of such groups include 2- and 3-benzofuryl, 2- and 3-benzothienyl, and 2- and 3-indolyl, and 2- and 3-quinolyl.

Suitable examples of groups or atoms for optional substitution especially of aryl and heteroaryl include one, two or three substituents independently selected from $C_{1-4}$ alkyl, $C_{1-4}$ alkoxy, halo (such as fluoro, chloro, bromo), hydroxy, nitro amino optionally substituted once or twice by $C_{1-4}$ alkyl, cyano and $SO_nH$, where n=0 to 2.

Preferably $R_1$ is cyano, acetyl, nitro and ethyl. Most preferably $R_1$ is acetyl or ethyl.

Preferably $R_2$ is hydrogen.

Preferably $R_3$ and $R_4$ are both methyl.

Preferably $R_5$ is hydroxy and $R_6$ and $R_9$ are hydrogen.

It should be appreciated that when $R_7$ is phenyl optionally independently substituted; this includes substitution by 1,2, 3,4 or 5 groups or atoms attached to the phenyl ring. Preferably there are 1 or 2 groups or atoms attached to the phenyl ring. The groups or atoms may be in any position around the phenyl ring. Likewise, it should be appreciated that when $R_7$ is heteroaryl optionally independently substituted; this includes substituents at any vacant positions around the heteroaryl moiety. Preferably there are 1 or 2 groups or atoms around the heteroaryl moiety, most preferably there is one group or atom around the heteroaryl moiety.

Preferably $R_7$ is 2,3- or 4-fluorophenyl, phenyl, 2 or 3-chlorophenyl, 2,3-dichlorophenyl, 2-trifluoromethylphenyl, 2-nitrophenyl, 2-aminophenyl, 2-chlorothiophen-3-yl, 3-chlorothiophen-2-yl or 3-chloro-4-fluorophenyl.

Preferably $R_7$ is fluorophenyl. More preferably $R_7$ is mono-fluorophenyl and even more preferably $R_7$ is 2-, 3 or 4-fluorophenyl. Most preferably $R_7$ is 4-fluorophenyl.

Preferably $R_8$ is hydrogen.

Preferably X is oxygen.

It should be appreciated that the compounds of formula (I) may have chiral carbon atoms at positions 2, 3 and 4 and therefore may exist as enantiomers. The present invention extends to each enantiomer and to mixtures thereof including racemates. It should further be appreciated that particular enantiomeric forms are preferred for different utilities, thus for utilities other than sub-arachnoid haemorrhage or neural shock the 3S, 4S enantiomers are preferred, however, for sub-arachnoid haemorrhage or neural shock the 3R, 4R enantiomers are preferred.

It should also be appreciated that certain $R_1$ substituents also have chiral centres and therefore may exist as enantiomers. The present invention extends to each enantiomer and to mixtures thereof including racemates It should be appreciated that the compound of formula (I) or a pharmaceutically acceptable salt thereof also includes solvates of such compounds, such as for example the hydrate.

The present invention further provides a compound of formula (I), or a pharmaceutically acceptable salt thereof as hereinbefore defined which exists predominently in the 3S, 4S enantiomeric form.

It should be appreciated that the term "exists predominently in the 3S, 4S enantiomeric form" means that there is greater than 50% of the 3S, 4S enantiomer present compared to the 3R, 4R enantiomer.

More preferably there is greater than 60% of the 3S, 4S enantiomer present, yet more peferably greater than 70% of the 3S, 4S enantiomer presence, even more preferably greater than 80% of the 3S, 4S enantiomer present and more preferably still greater than 90% of the 3S, 4S enantiomer present. Most preferably there is greater than 95% of the 3S, 4S enantiomer compound to the 3R, 4R enantiomer.

Example of compounds of formula (I) are:

cis-(±)-6-Acetyl-4-(4-fluorobenzoylamino)-3,4-dihydro-2,2-dimethyl-2H-1-benzopyran-3-ol, cis-6-Acetyl-4R-(4-fluorobenzoylamino)-3,4-dihydro-2,2-dimethyl-2H-1-benzopyran-3R-ol, cis-6-Acetyl-4S-(4-fluorobenzoylamino)-3,4-dihydro-2,2-dimethyl-2H-1-benzopyran-3S-ol, cis-6-Cyano-4R-(4-fluorobenzoylamino)-3,4-dihydro-2,2-dimethyl-2H-1-benzopyran-3R-ol, cis-6-Cyano-4S-(4-fluorobenzoylamino)-3,4-dihydro-2,2-dimethyl-2H-1-benzopyian-3S-ol, cis-6-Ethyl-4R-(4-fluorobenzoylamino)-3,4-dihydro-2,2-dimethyl-2H-1-benzopyran-3R-ol, cis-6-Ethyl-4S-(4-fluorobenzoylamino)-3,4-dihydro-2,2-dimethyl-2H-1-benzopyran-3S-ol, cis-6-Acetyl-4S-(2-chlorobenzoylamino)-3,4-dihydro-2,2-dimethyl-2H-1-benzopyran-3S-ol, cis-6-Acetyl-4S-(benzoylamino)-3,4-dihydro-2,2-dimethyl-2H-1-benzopyran-3S-ol, cis-6-Acetyl-4S-(2-methylbenzoylamino)-3,4-dihydro-2,2-dimethyl-2H-1-benzopyran-3S-ol, cis-6-Acetyl-4-(2,3-dichlorobenzoylamino)-3,4-dihydro-2,2-dimethyl-2H-1-benzopyran-3-ol, cis-6-Acetyl-4S-(2-trifluoromethylbenzoylamino)-3,4-dihydro-2,2-dimethyl-2H-1-benzopyran-3S-ol, cis-6-Cyano-4R-(3-fluorobenzoylamnino)-3,4-dihydro-2,2-dimethyl-2H-1-benzopyran-3R-ol, cis-4-(4-fluorobenzoylamino)-3,4-dihydro-2,2-dimethyl-6-nitro-2H-1-benzopyran-3-ol, cis-6-Acetyl-4S-(2-fluorobenzoylamino)-3,4-dihydro-2,2-dimethyl-2H-1-benzopyran-3S-ol, cis-6-Acetyl-4S-(3-fluorobenzoylamino)-3,4-dihydro-2,2-dimethyl-2H-1-benzopyran-3S-ol, cis-6-Acetyl-4S-(2-nitrobenzoylamino)-3,4-dihydro-2,2-dimethyl-2H-1-benzopyran-3S-ol, cis-6-Acetyl-4S-(2-aminobenzoylamino)-3,4-dihydro-2,2-dimethyl-2H-1-benzopyran-3S-ol, cis-6-Acetyl-4S-(3-chlorobenzoylamino)-3,4-dihydro-2,2-dimethyl-2H-1-benzopyran-3S-ol, cis-6-Aceryl-4S-(2-chlorothiophen-3-carbonylamino)-3,
4-dihydro-2,2-dimethyl-2H-1-benzopyran-3S-ol cis-6-Cyano-4-(benzoylamino)-3,4-dihydro-2,2-
dimethyl-2H-1-benzopyran-3-ol cis-6-Acetyl-4S-(3-chlorothiophen-2-carbonyl)-3,4-
dihydro-2,2-dimethyl-2H-1-benzopyran-3-ol and cis-6-Acetyl-4S-(2-chloro-4-fluorobenzoylamino)-3,4-
dihydro-2,2-dimethyl-2H-1-benzopyran-3-ol Such compounds except for racemic cis-6-Cyano-4-(benzoylamino)-3,4-dihydro-2,2-dimethyl-2H-1-benzopyran-3-ol and pharmaceutically acceptable salt thereof are believed to be novel and form a preferred aspect of the present invention.

The administration to the mammal may be by way of oral or parenteral administration.

An amount effective to treat the disorders hereinbefore described depends on the usual factors such as the nature and severity of the disorders being treated and the weight of the mammal. However, a unit dose will normally contain 1 to 1000 mg, suitably 1 to 500 mg, for example an amount in the range of from 2 to 400 mg such as 2, 5, 10, 20, 30, 40, 50, 100, 200, 300 and 400 mg of the active compound. Unit doses will normally be administered once or more than once per day, for example 1, 2, 3, 4, 5 or 6 times a day, more usually 1 to 4 times a day, such that the total daily dose is normally in the range, for a 70 kg adult of 1 to 1000 mg, for example 1 to 500 mg, that is in the range of approximately 0.01 to 15 mg/kg/day, more usually 0.1 to 6 mg/kg/day, for example 1 to 6 mg/kg/day.

It is greatly preferred that the compound of formula (I) is administered in the form of a unit-dose composition, such as a unit dose oral, rectal, topical or parenteral (especially intravenous) composition.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavoring or coloring agents.

Oral formulations also include conventional sustained release formulations, such as tablets or granules having an enteric coating.

For parenteral administration, fluid unit dose forms are prepared containing the compound and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

As is common practice, the compositions will usually be accompanied by written or printed directions for use in the medical treatment concerned.

The present invention further provides a pharmaceutical composition for use in the treatment and/or prophylaxis of anxiety, mania, depression, disorders associated with a subarachnoid haemorrhage or neural shock, the effects associated with withdrawal from substances of abuse such as cocaine, nicotine, alcohol and benzodiazepines, disorders treatable or preventable with anti-convulsive agents, such as epilepsy, Parkinson's disease, psychosis, migraine and/or Cerebral ischaemia, which comprises a compound of formula (I) (including racemic cis-4-benzoylamino-6-cyano-3,4-dihydro-2,2-dimethyl-2H-benzo[b]pyran-3-ol), or a pharmaceutically acceptable salt thereof, and a pharmaceutically acceptable carrier.

The present invention also provides a method of treatment and/or prophylaxis of anxiety, mania, depression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy Parkinson's disease, psychosis, migraine and/or Cerebral ischaemia, comprising administering to the sufferer in need thereof an effective or prophylactic amount of a compound of formula (I) including cis-4-benzoylamino-6-cyano-3,4-dihydro-2,2-dimethyl-2H-benzo[b]pyran-3-ol, or a pharmaceutically acceptable salt thereof.

In a further aspect the invention provides the use of a compound of formula (I) including (racemic cis-4-benzoylamino-6-cyano-3,4-dihydro-2,2-dimethyl-2H-benzo[b]pyran-3-ol), or a pharmaceutically acceptable salt thereof, for the manufacture of a medicament for the treatment and/or prophylaxis of anxiety, mania, depression, disorders associated with a subarachnoid haemorrhage or neural shock, the effects associated with withdrawal from substances of abuse such as cocaine, nicotine, alcohol and benzodiazepines, disorders treatable or preventable with anti-convulsive agents, such as epilepsy; Parkinson's disease, psychosis, migraine and/or cerebral ischaemia.

In a further aspect the present invention provides a pharmaceutical composition containing a compound of formula (I) (not including racemic cis-4-benzoylamino-6-cyano-3,4-dihydro-2,2-dimethyl-2H-benzo[b]pyran-3-ol), or a pharmaceutically acceptable salt thereof and a pharmaceutically acceptable carrier.

In a further aspect the invention provides the use of a compound of formula (I) (not including racemic cis-4-benzoylamino-6-cyano-3,4-dihydro-2,2-dimethyl-2H-benzo[b]pyran-3-ol), or a pharmaceutically acceptable salt thereof as a therapeutic agent, in particular for the treatment and/or prophylaxis of anxiety, mania, depression, disorders associated with a sub-arachnoid haemorrhage, neural shock, the effects associated with withdrawal from substances of abuse such as cocaine, nicotine, alcohol and benzodiazepines; disorders treatable or preventable with anti-convulsive agents, such as epilepsy; Parkinson's disease, pychosis, mgraine and/or cerebral ischaemia.

Such compositions may be prepared in the manner as hereinbefore described.

Generally, compounds of formula (I) may be prepared from the corresponding trans compounds, procedures for the preparation of which are generally described in EP-0126311, EP-0376524, EP-205292, EP-0250077, EP-0093535, EP-0150202, EP-0076075, WO/89/05808, EP-0350805, EP-0277611, EP-0277612, EP-0337179, EP-0339562, EP-0355565, EP-A-415 065 (E. Merck), EP-A-450 415 (Squibb) EP-0466131, EP-A-0482934, EP-A-0296975, JO-2004-791 and WO\89\07103.

The cis compounds may be prepared by procedures generally described in or analogous to those described in EP-A-0139992.

Compounds of formula (I) may also be prepared according to the procedures described by G. Burrell et al, Tet. Letters, 31, 3649–3652 (1990) or by the procedures described by U. Quast and E. Villhauer, Eur. J. Pharmacol, Molecular Pharmacology Section 245, 165–171 (1993).

A further aspect of the present invention provides a process for the preparation of a compound of formula (I) (not including cis-4-benzoylamino-6-cyano-3,4-dihydro-2,2-dimethyl-2H-benzo[b]pyran-3-ol) or a pharmaceutically acceptable salt thereof, which comprises treating the corresponding trans compound in which $R_5$ is hydroxy and $R_8$ is hydrogen, with tifluoromethane sulphonic anhydride in a suitable solvent such as pyridine to furnish the cis-oxazoline compound of formula (II);

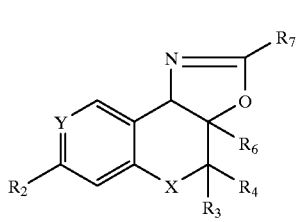

(II)

in which all the variables are as defined in relation to formula (I), followed by (i) acid treatment using, for example, dilute sulphuric acid and (ii) by base treatment, for example, using sodium bicarbonate solution to give the cis compound of formula (I) and thereafter if desired and in appropriate order separating any enantiomers, converting $R_5$ hydroxy to other values of $R_5$ and/or $R_8$ hydrogen to other values of $R_8$ and/or forming a pharmaceutically acceptable salt thereof.

It should be appreciated that the cis-oxazoline compounds of formula (II) other than the oxazoline of racemic cis-4-benzoylamino-6-cyano, 3-4-dihydro-2,2-dimethyl 2H-benzo [b]pyran-3-ol are novel and therefore form a further aspect of the present invention.

Conversions of $R_5$ hydroxy and $R_8$ respectively may be carried out, using conventional procedures in the art, in particular using the procedures outlined in the aforementioned patents.

It should be appreciated that racemates for formula (I) may be resolved or enantiomerically purified compounds of formula (I) may be prepared using procedures conventional in the art and in particular using the procedures outlined in EP-0430631 and EP-0355584.

It should also be appreciated that it is preferred that the compounds of formula (I) may be prepared in the required enantiomeric form by forming a chirally pure epoxide using catalysts and conditions generally outlined in WO91\14694 or WO 93\17026 and thereafter converting the epoxides to the required compound of formula (I) using procedures outlined herein.

The trans compounds of formula (I) may be prepared according to the procedures outlined in PCT/GB92/01045 which procedures are incorporated herein by reference or the trans compounds of formula (I) may be prepared according to methods analogous to these described in the one mentioned patents.

The trans compounds of formula (I) in which $R_5$ is hydroxy, $R_6$ is $C_{1-2}$ alkyl and $R_9$ is hydrogen may be prepared according to the procedures outlined in R. Gericke et al. J. Med. Chem. Vol.34, p3074(1991).

The following compounds were prepared by methods analgous to those described in the abovementioned patents publications.

The following descriptions, examples and pharmacological test results illustrate the present invention:

Description 1 cis-(±)-8-Acetyl-2-(4-fluorophenyl)-3a,9b-dihydro-4,4 dimethyl-4H-1-benzopyrano[4,3-d]oxazole trans-(±)-6-Acetyl-4-(4-fluorobenzoylamino)-3-4-dihydro-2,2-dimethyl-2H-1-benzopyran-3-ol (example 13 of EP 0 126 311 B 1, 2.0 g) was dissolved in pyridine (30 ml) and the solution stirred at −5 to 0° C. under nitrogen. Trifluoromethane sulphonic anhydride (1.74 g) was added dropwise to the stirred solution during 10 minutes. The resulting mixture was stirred at room temperature for 18 hours. The pyridine was evaporated in vacuo and water (50 ml) added to the residue. The solution was extracted with dichloromethane (50 ml) and the organic layer was washed with brine (50 ml) and dried over anh. $MgSO_4$. Filtration and evaporation gave a crude product which was recrystallised from ethyl acetate-hexane to give the title oxazoline as a white solid (1.222 g) of mp 185–186° C.

NMR (DMSO $d_6$) δ: 1.30 (s, 3H), 1.56 (s, 3H), 2.55 (s, 3H), 5.05 (d, J=10 Hz, 1H), 5.48 (d, J=10 Hz, 1 h), 6.93 (d, J=8 Hz, 1H), 7.22 (m, 2H), 7.82 (dd, J=10, 2 Hz, 1H), 7.93 (m, 2H), 8.05 (d, J=2 Hz, 1H). Mass spectrum: m/z 339, 324, 268, 123; IR (nujol): 1640, 1670 $cm^{-1}$.

Description 2 cis-(±)-6-Acetyl-4-amino-3-(4-fluorobenzoyloxy)-3,4-dihydro-2,2-dimethyl-2H-1-benzopyran sulphate cis (±)-Oxazoline (500 mg) was dissolved in 1,4-dioxane (40 ml), water (15 ml) and 5N $H_2SO_4$ (12 drops). The resulting mixture was allowed to stir at room temperature for 2 days. The 1,4-dioxane was evaporated under vacuum at 30° C. and the product extracted with ethyl acetate (2×50 mls). The organic layer was washed with brine (50 mls), dried (MgSO$_4$), filtered and evaporated. The residual material (500 mg) was recrystallised twice from acetone/hexane to give (260 mg) of the amino ester salt as a white crystalline salt m.p. 187° C.

NMR (DMSO d$_6$) δ: 1.30 (s, 3H), 1.40 (s, 3H), 2.55 (s, 3H), 5.10 (d, J=4 Hz, 1H), 5.60 (d, J=4 Hz, 1H), 7.02 (d, J=7 Hz, 1H), 7.33 (m, 2H), 7.90 (m, 3H), 8.48 (s, 1H), 8.98 (br s, 2H). Mass spectrum: m/z 339, 324, 268, 163, 148, 123. IR: 1681, 1732 cm$^{-1}$.

EXAMPLE 1 cis-(±)-6-Acetyl-4-(4-fluorobenzoylamino)-3,4-dihydro-2,2-dimethyl-2H-1-benzopyran-3-ol The amino ester compound (260 mg) was dissoved in 1,4-dioxane (30 ml) and water (20 ml) and NaHCO$_3$ (solid) added until the pH was 8. The 1,4-diozane was evaporated under vacuum at 40° C. The product was extracted with ethyl acetate (2×50 ml), dried (MgSO$_4$), filtered and evaporated. The residual material (250 mg) obtained, was recrystallised from acetone/hexane to give (150 mg) of the cis (±) benzamide as a white crystalline solid m.p. 190° C.

NMR (DMSO) δ: 1.30 (s, 3H), 1.42 (s, 3H), 2.45 (s, 3H), 3.72 (m, 1H), 5.5 (d, J=9.5 Hz, 1H), 5.64 (d, J=5 Hz, 1H), 7.32 (m, 2H), 7.77 (m, 2H), 8.10 (m, 2H), 8.53 (d, J=10 Hz, 1H). Mass Spectrum: m/z 358, 339, 324, 203, 123. IR (Nujol): 1620, 1667, 3360, 3400 cm$^{-1}$.

The following examples were prepared in an analogous manner to the compound of example 1, from the appropriate trans compounds.

EXAMPLE 2 cis-6-Acetyl-4R-(4-fluorobenzoylamino)-3,4-dihydro-2,2-dimethyl-2H-1-benzopyran-3R-ol m.p. 161° C.; $[\alpha]_D^{25}$ +107.3°, MeOH (c=1.0)

EXAMPLE 3 cis-6-Acetyl-4S-(4-fluorobenzoylamino)-3,4-dihydro-2,2-dimethyl-2H-1-benzopyran-3S-ol m.p. 161° C.; $[\alpha]_D^{25}$ −106.1°, MeOH (c=1.0)

EXAMPLE 4 cis-6-Cyano-4R-(4-fluorobenzoylamino)-3,4-dihydro-2,2-dimethyl-2H-1-benzopyran-3R-ol m.p. 105–106° C.; $[\alpha]_D^{25}$ +86.9°, MeOH (c=1.0)

EXAMPLE 5 cis-6-Cyano-4S-(4-fluorobenzoylamino)-3,4-dihydro-2,2-dimethyl-2H-1-benzopyran-3S-ol m.p. 102–105° C.; $[\alpha]_D^{25}$ −79.9°, MeOH (c=1.0)

EXAMPLE 6 cis-6-Ethyl-4R-(4-fluorobenzoylamino)-3,4-dihydro-2,2-dimethyl-2H-1-benzopyran-3R-ol m.p. 130° C.; $[\alpha]_D^{25}$ +51.4°, MeOH (c=1.0)

EXAMPLE 7 cis-6-Ethyl-4S-(4-fluorobenzoylamino)-3,4-dihydro-2,2-dimethyl-2H-1-benzopyran-3S-ol m.p. 130° C. $[\alpha]^{20}_D$ −40.1° (meOH, c=1.0)

EXAMPLE 8 cis-6-Acetyl-4S-(2-chlorobenzoylamino)-3,4-dihydro-2,2-dimethyl-2H-1-benzopyran-3S-ol mp 176° C.; $[\alpha]_D^{25}$ −22.7°, MeOH (c=1.0)

EXAMPLE 9 cis-6-Acetyl-4S-(benzoylamino)-3,4-dihydro-2,2-dimethyl-2H-1-benzopyran-3S-ol

EXAMPLE 10 cis-6-Acetyl-4S-(2-methylbenzoylamino)-3,4-dihydro-2,2-dimethyl-2H-1-benzopyran-3S-ol

EXAMPLE 11 cis-6-Acetyl-4-(2,3-dichlorobenzoylamino)-3,4-dihydro-2,2-dimethyl-2H-1-benzopyran-3-ol

EXAMPLE 12 cis-6-Acetyl-4S-(2-trifluoromethylbenzoylamino)-3,4-dihydro-2,2-dimethyl-2H-1-benzopyran-3S-ol

EXAMPLE 13 cis-6-Cyano-4R-(3-fluorobenzoylamino)-3,4-dihydro-2,2-dimethyl-2H-1-benzopyran-3R-ol

EXAMPLE 14 cis-4-(4-fluorobenzoylamino)-3,4-dihydro-2,2-dimethyl-6-nitro-2H-1-benzopyran-3-ol

EXAMPLE 15 cis-6-Acetyl-4S-(2-fluorobenzoylamino)-3,4-dihydro-2,2-dimethyl-2H-1-benzopyran-3S-ol

EXAMPLE 16 cis-6-Acetyl-4S-(3-fluorobenzoylamino)-3,4-dihydro-2,2-dimethyl-2H-1-benzopyran-3S-ol

EXAMPLE 17 cis-6-Acetyl-4S-(2-nitrobenzoylamino)-3,4-dihydro-2,2-dimethyl-2H-1-benzopyran-3S-ol

EXAMPLE 18 cis-6-Acetyl-4S-(2-aminobenzoylamino)-3,4-dihydro-2,2-dimethyl-2H-1-benzopyran-3S-ol

EXAMPLE 19 cis-6-Acetyl-4S-(3-chlorobenzoylamino)-3,4-dihydro-2,2-dimethyl-2H-1-benzopyran-3S-ol mpt 110° C., $[\alpha]_D^{25}$ −105.7°, (MeOH c=1.01)

EXAMPLE 20 cis-6-Acetyl-4S-(2-chlorothiophen-3-carbonylamino)-3,4-dihydro-2,2-dimethyl-2H-1-benzopyran-3S-ol

EXAMPLE 21 cis-6-Cyano-4-(benzoylamino)-3,4-dihydro-2,2-dimethyl-2H-1-benzopyran-3-ol

The compound was prepared as described for example 3 of U.S. Pat. No. 4,687,779 (1987).

EXAMPLE 22 cis-6-Acetyl-4S-(3-chlorothiophen-2-carbonyl)-3,4-dihydro-2,2-dimethyl-2H-1-benzopyran-3-ol

EXAMPLE 23 cis-6-Acetyl-4S-(2-chloro-4-fluorobenzoylamino)-3,4-dihydro-2,2-dimethyl-2H-1-benzopyran-3-ol mpt 189° C.;

PHARMACOLOGICAL DATA

1. Rat Social Interaction Test

The compounds of formula (I) including cis-4-benzoylamino-6-cyano-3,4-dihydro-2,2-dimethyl-2H-benzo[b]pyran-3-ol or pharmaceutically acceptable salts thereof may be tested for therapeutic utility using the procedure outlined as follows:

Potential anxiolytic properties are evaluated using the rat social interaction procedure based on that originally described by File (1980, J. Neurosci. Methods, 2, 219–238). In this model anxiolytic agents selectively increase social interaction independently of any effect on locomotor activity.

Method

Male Sprague—Dawley rats (Charles River, U.K., 250–300 g) are singly housed for 3 days prior to testing. On the test day, the animals are then randomly assigned to groups of 8–16 and dosed orally at a dose volume of 1 ml/kg with various doses of compound (1–300 mg/kg) or vehicle. At 60 min post dose the rats are placed with a weight- and treatment-matched pair male (encountered for the first time) in the social interaction box under high-light, unfamiliar conditions. The box is made of white perspex 54×37×26 cm with a transparent perspex front side. The floor is divided into 24 equal squares and is brightly lit (115 lux). Time spent (secs) in active social interaction (sniffing, grooming, following, mounting, climbing over or under, boxing, biting) is scored "blind" by remote monitoring as is the number of squares crossed (as an index of locomotion).

The mean and standard error for time spent in social interaction and number of squares crossed are then calculated for each particular treatment group and drug-induced changes are expressed as a percentage increase or decrease from control values. Statistical comparisons are made between vehicle- and drug-treated groups using Dunnett's multiple comparisons procedure following significant one way analysis of varience.

Drugs are suspended in 1% methyl cellulose.

2. Mes Test

The maximal electroshock seizure (MES) threshold test in rodents is particularly sensitive for detecting potential anticonvulsant properties[1]. In this model, anticonvulsant agents elevate the threshold to electrically-induced seizures whilst proconvulsants lower the seizure threshold.

Method

Mice (male, Charles River, U.K. CD-1 strain, 25–30 g) are randomly assigned to groups of 10–20 and dosed orally or intraperitoneally at a dose volume of 10 ml/kg with various doses of compound (0.3–300 mg/kg) or vehicle. Mice are then subjected at 30 or 60 min post dose to a single electroshock (0.1 sec, 50 Hz, sine wave form) administered via corneal electrodes. The mean current and standard error required to induce a tonic seizure in 50% ($CC_{50}$) of the mice in a particular treatment group is determined by the 'up and down' method of Dixon and Mood (1948)[2]. Stastical comparisons between vehicle- and drug-treated groups are made using the method of Litchfield and Wilcoxon (1949)[3].

In control animals the $CC_{50}$ is usually 14–18 mA. Hence the first animal in the control group is subjected to a current of 16 mA. If a tonic seizure does not ensue, the current is increased for a subsequent mouse. If a tonic convulsion does occur, then the current is decreased, and so on until all the animals in the group have been tested.

The percentage increase or decrease in $CC_{50}$ for each group compared to the control is calculated.

Studies are carried out using a Hugo Sachs Electronik Constant Current Shock Generator with totally variable control of shock level from 0 to 300 mA and steps of 2 mA are usually used.

Drugs are suspended in 1% methyl cellulose.

References
1. Loscher, W. and Schmidt, D. (1988). Epilepsy Res., 2, 145–181
2. Dixon, W. J. and Mood, A. M. (1948). J. Amer. Stat. Assn., 43, 109–126
3. Litchfield, J. T. and Wilcoxon, F.(1949). J. Pharmacol. exp. Ther., 96, 99–113

Results

The compound of example 7 enhanced seizure threshold by 105% at 10 mg/kg p.o. and the compound of example 3 enhanced seizure threshold by 84% at 10 mg/kg p.o.

3. X-Maze

The compounds of formula (I) including cis-4-benzoylamino-6-cyano-3,4-dihydro-2,2-dimethyl-2H-benzo[b]pyran-3-ol or pharmaceutically acceptable salts thereof may be tested for therapeutic utility using the procedure outlined as follows:

Introduction

The X-maze test of anxiety (Handley and Mithani, 1984) examines the exploratory response of naive rats in an environment which offers both anxiogenic (open arms) and relatively non-anxiogenic (closed arms) areas. A selective increase in exploration of the open arms following drug pretreatment is therefore postulated to indicate anxiolytic effects.

Method

The X-maze was raised 70 cm above the floor and consisted of two enclosed arms 45 cm (long)×15 cm (wide)× 10 cm (high) and two open arms 45×10×1 cm arranged such that the two arms of each type were opposite each other. Both arm types are marked into two equal sections. Rats are placed onto the centre of the X-maze and observed for a period of 10 minutes during which time the following parameters were recorded: 1) the number of entries onto, and the time spent on, (a) open arms, (b) closed arms, (c) end of open arms and (d) end of closed arms. 2) the number of sections crossed. The fear-drive evoked in the open arms exceeds that in the enclosed arms and rats typically show a clear preference for the enclosed arms. Anxiolytic drugs increase the number of entries made onto, and the time spent on, the outer half of the open arms, and also the percentage of entries made onto, and the time spent on, the whole of the open arms. These four measures of anxiety, and also the total number of sections traversed, were calculated for each animal. Drugs are administered intraperitoneally or orally to groups of 6 to 12 rats 30 to 60 mins before testing. Statistical comparisons between vehicle- and drug-treated groups were made using a Mann-Whitney 'A' test (two tailed).

S. L. Handley and S. Mithani, Arch. Pharmacol., 1984 327 1–5

4. Mongrel Dog Delayed Cerebral Vasospasm

The compounds of formula (I) including cis-4-benzoylamino-6-cyano-3,4-dihydro-2,2-dimethyl-2H-benzo[b]pyran-3-ol or pharmaceutically acceptable salts thereof may be tested for therapeutic utility using the procedures outlined as follows:

Twenty-five male mongrel dogs, weighing 9–12 kg, are used in these studies. The animals are housed and cared for in accordance with the Guide for the Care and Use of Laboratory Animals [DHEW (DHHS) publication No. (NIH) 85-23, revised 1985]. All procedures using laboratory animals are approved by the Institutional Animal Care and Use Committee of SmithKline Beecham Pharmaceutical. Each animal is anaesthetized with pentobarbital (35 mg/kg, iv) and placed on a heated operating table in the supine position. All animals are then tracheotomized, paralyzed (tubocurarine; 0.1 mg/kg, i.v.) and artificially ventilated with room air. End-tidal $CO_2$ (et $CO_2$) is monitored continuously and arterial blood gas analysis was performed periodically to assure stable and adequate ventilation throughout each experiment. Polyethylene cannulae are placed in the left external jugular vein and the right femoral artery and vein for drug administration, monitoring arterial blood pressure, and blood sampling, respectively. Transfemoral catheterization of the left vertebral artery is then performed via the left femoral artery using a 5 french Lehman dacron catheter (Bard, Tewksbury Mass.). Anaesthesia is supplemented as needed with pentobarbital (5 mg/kg, i.v.) prior to the experimental period.

The effects of the compounds of this invention on acute cerebral vasospasm are evaluated in 15 dogs. In all animals a control digital subtraction angiogram of the anterior spinal artery and basilar artery is obtained following the intravertebral injection of radiocontrast material (Omnipaque 300). In each dog, 4 mls of cerebrospinal fluid is then removed from the dorsal cistern via needle puncture of the atlantoocipital membrane and 4 mls of autologous venous blood was injected. An angiogram is then repeated in each dog 30 minutes following the intracisternal administration of blood and an acute vasospasm of the basilar and anterior spinal arteries is identified and quantitated. The infusion of vehicle (10% polyethylene glycol 200) for 30 minutes has no effect on the acute vasospasm. The effect of a 30 minute infusion of test compounds on the reversal of acute vasospasm is observed in the basilar and anterior spinal arteries.

The effects of the compounds of this invention are also examined in the chronic canine model of delayed cerebral vasospasm (two haemorrhage model of cerebral vasospasm). In this model, a control vertebral angiogram is obtained and autologous blood is administered intracisternally on day 1 (as above). On day 3 the intracisternal administration of blood is repeated and the severe delayed vasospasm is quantitated angiographically on day 7 in all animals. The infusion of vehicle (10% polyethylene glycol 200) for 60 minutes has no effect on the delayed vasospasm observed in the basilar and anterior spinal arteries (n=5). The effect of an infusion of test compounds on the reversal of significantly delayed cerebral vasospasm indicates that the compound is active.

5. The compounds of formula (I) including cis-4-benzoylamino-6-cyano-3,4-dihydro-2,2-dimethyl-2H-benzo[b]pyran-3-ol or pharmaceutically acceptable salts thereof may be tested for therapeutic utility using the procedures outlined as follows:

1) Anti-Parkinsonian Activity 6-Hydroxydopamine-lesioned rat model

The above test as described by Ungerstedt, U, 1971, Acta Physiol. Scand 367, 49–68, and/or Ungerstedt, U, 1971, Acta Physiol Scand. 367, 69–93, may be used to determine the anti-Parkinsonian activity of compounds of formula(I) including cis-4-benzoylamino-6-cyano-3,4-dihydro-2,2-dimethyl-2H-benzo[b]pyran-3-ol or pharmaceutically acceptable salts thereof.

2) Anti-Psychotic Activity Amphetamine-induced rat hyperlocomotion model

The above test as described by Kokkindis L, and Anisman, M, 1980, Psychological Bulletin, 88, 551–579, may be used to determine the anti-psychotic activity of compounds of formula (I) including cis-4-benzoylamino-6cyano-3,4-dihydro-2,2-dimethyl-2H-benzo[b]pyran-3-ol or pharmaceutically acceptable salts thereof.

3) Anti-Migraine Activity Cortical Spreading Depression and Migraine

The above test as described by Wahl et al, 1987, Brain Research, 411, 72–80 may be used to determine the anti-migraine activity of compounds of formula (I) including cis-4-benzoylamino-6-cyano-3,4-dihydro-2,2-dimethyl-2H-benzo[b]pyran-3-ol or pharmaceutically acceptable salts thereof.

4) Cerebral ischaemia a) Mongolian Gerbil Test

The in vivo experiments are carried out on adult Mongolian gerbils (Tumblebrook Farm (MA). weighing 60–80 g. Transient forebrain ischemia is produced by bilateral carotid artery ligation under 2.5% isoflourane in 100% $O_2$ anesthesia, the animals being placed onto a heating pad to maintain body temperature at 37° C. The common carotid arteries are exposed and aneurism clips are placed on both arteries for a certain period of time indicated in the figure legends. PBN dissolved in saline was administered intraperitoneally as a bolus 30 min before occlusion (pretreatments) or immediately after and again at 6 h of reperfusion, followed by the same dose b.i.d. for 2 days (post-treatment). For quantification of CA1 neurons, animals are sacrificed at 7 days postischemia and perfused with buffered formalin. Brains were removed, stored in formalin for 3 days, embedded in paraffin, cut at 7-$\mu$m-thick coronal sections (1.5–1.9 mm posterior to bregma[15]) and stained with thionin. The number of intact neurons over a 750-$\mu$m length of the CA1 layer on both hippocampal sides of 3 sections is counted for each animal.

b) MCAO Method

Three strains of mature male rats (SHR) are obtained from commercial vendors (Taconic Farms, Germantown, N.Y.; Charles River, Danvers, Mass.; and Charles River, respectively) at 18 wk of age (250–300 g in weight) and are housed for 2 to 4 weeks prior to utilization in these studies. In order to verify that the strains of animals studied are indeed hypertensive and normotensive, groups of animals from each strain are anesthetized with 2% isoflourane (Anaquest, Madison, Wis.) and chronically prepared under aseptic conditions for recording of blood pressure. The femoral artery is cannulated with polyethylene tubing (PE60; Clay Adams. Parsippany, N.J.) extending just into the descending aorta. The tubing is lead subdermally from the artery and exteriorized between the scapula just below the back of the neck and cleared/filled with sterile isotonic saline. Incisions are closed using 2-0 silk suture and treated with 5% lidocaine ointment (Astra Pharmaceuticals, Westborough, Mass.) Animals recover from surgery/anesthesia within 5 min. Mean arterial blook pressures are recorded 4 to 5 h after surgery for 5 min/rat by connecting the exteriorized tubing in each rat to a Statham pressure transducer (P2.3Db; Statham Medical Instruments. Los Angeles, Calif.) with output to a polygraph (Model R711: Beckman Instruments, Inc., Fullerton. Calif.).

Focal Stroke Procedure

MCAO or sham surgery is carried out in the SHR, SD rats under sodium pentobarbital (65 mg/kg, i.p. and supplemented as needed) anesthesia. All animals are allowed free access to food and water prior to and after surgery. Body temperature is maintained at 37° C. using a heating pad throughout the surgical procedure. Surgery is conducted similar to that described previously (2.4). The right dorsal surface to the head and shaved and prepped with providone-iodine, and the rat placed in a stereotaxic device (David Kopf Instruments, Tujunga, Calif.) with the surgery (right) side of the head superior. A 1–2 cm incision was made between the orbit and the external auditory canal. The temporal muscle is dissected from the skull and retracted without damaging the zygomatic bond or mandibular nerve. Under an operating microscope and with saline irrigation, a 2–3 mm craniotomy is made just rostral to the zygomatic-squamosal skull suture. The dura is opened over the artery using the modified tip of a 30-gauge needle. For permanent right MCAO, using electrocoagulation (Force 2 Electrosurgical Generator, Valley Lab Inc., Boulder, Colo.), the artery was stimultaneously occluded and cut dorsal to the lateral olfactory tract at the level of the inferior cerebral vain. A small piece of sterile saline-soaked Gelfoam (Upjohn, Kalamazoo, Mich.) is then positioned over the craniotomy and the temporails muscle and skin are closed in two layers. Animals are allowed to recover from anesthesia under a heating lamp and then are returned to their cages. The animals are sacrificed 24 hours following MCAO and the brains are prepared from reactive histologic examination.

Measurements of Ischemic Damage

Following the neurologic evaluation (24 hours after surgery) rats are euthanized with an overdose of sodium pentobarbital. Within 2–3 min, brains are removed and six coronal forebrain slices (2 mm thick) are made from the level of the olfactory bulbs to the cortical-cerebellar junction using a rat brain slicer [(59); Zivic-Miller Laboratories Inc., Allison Park, Pa.]. These forebrain slices then are immersed immediately in a 1% solution of triphenyltetrazolium chloride (TTC) in phosphate buffer at 37° C. for 20–30 min (6.78). Strained tissues then are fixed by filtration in 10% phosphate buffered formalin. The two sides of each TTC-strained section are photographed in color using a polaroid camera. These photographs are analyzed for the quantification of ischemic damage using an image analysis system (Amersham RAS 3000; Loats Associates, Inc.). Morphological changes following surgery are evaluated in the entire forebrain (total of 11 planar surfaces) for each animal. The 11 planar images are planar surfaces) for each animal. The 11 planar images were obtained from each side of the six 2 mm thick sections and correspond approximately to 1 mm section surfaces from +5 mm to −5 mm from bregma (97) and include the complete forebrain. These planar image surfaces (from the photographs) are digitized and used in the Image Analysis System for planimetry determination of infarct size and swelling. Two parameters of ischemic damage due to MCAO are determined for each slice as described previously (2,4,98, 122). "Hemispheric swelling" is expressed as the percent increase in size of the ipsilateral (i.e., surgery side) hemisphere over the contralateral (normal) hemisphere and is calculated as:

$$\text{Percent Hemispheric Swelling} = \frac{\text{Ipsilateral Hemisphere Area} - \text{Contralateral Hemisphere Area}}{\text{Contralateral Hemisphere Area}} \times 100$$

"Infarct size" which was expressed as the percent infarcted tissue in reference to the contralateral (normal) hemisphere and is calculated as:

$$\text{Percent Hemispheric Infarct Size} = \frac{\text{Infarct area}}{\text{Contralateral Hemisphere Area}} \times 100$$

The swelling and infarct size are expressed in reference to the contralateral hemisphere (i.e., ipsilateral ischemic damage is normalized to the normal contralateral hemisphere). These parameters are determined for each slice to evaluate the profile of damage throughout the forebrain (i.e., "fore-brain profile") and for "total" forebrain changes by using the sum of all individual slice data in these formulas.

The occurrence of brain edema asociated with hemispheric swelling following MCAO was determined by comparison of wet/dry weight as described previously (45,118). Rats were sacrificed by an overdose of sodium pentobarbital 24 hours after sham or MCAO surgery. The brains are quickly removed, the forebrain isolated at the cerebellar cortical junction and cut into two hemispheres, and each forebrain hemisphere measured on a Mettler Types H5 chemical balance (Mettler Instruments Corp, Hightstown, N.J.) within 2 min after decapitation. The dry weight was measured on the same scale after drying the hemisphere in an over at 80° C. for 48–72 hours. The water content of each hemisphere was calculated as the difference between the wet and dry weight as a percent fraction from the wet weight:

$$\text{Percent Water Content} = \frac{\text{Wet Weight} - \text{Dry Weight}}{\text{Wet Weight}} \times 100$$

We claim:

1. A method of treatment of anxiety mania, depression, disorders associated with a subarachnoid haemorrhage, neural shock, the effects associated with withdrawal from substances of abuse, disorders treatable with anti-convulsive agents, Parkinson's disease, psychosis, migraine and/or cerebral ischaemia, comprising administering to the sufferer in need thereof an effective or prophylactic amount of a compound of formula (I) or a pharmaceutically acceptable salt thereof:

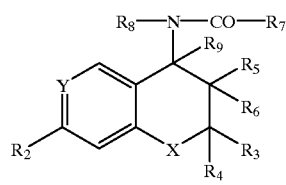

(I)

wherein:

Y is C—$R_1$;

$R_1$ is acetyl;

$R_2$ is hydrogen, $C_{3-8}$ cycloalkyl, $C_{1-6}$ alkyl optionally interrupted by oxygen or substituted by hydroxy, $C_{1-6}$ alkoxy or substituted aminocarbonyl, $C_{1-6}$ alkylcarbonyl, $C_{1-6}$ alkoxycarbonyl, $C_{1-6}$ alkylcarbonyloxy, $C_{1-6}$ alkoxy, nitro, cyano, halo, trifluoromethyl, or $CF_3S$; or a group $CF_3$—A—, where A is —$CF_2$—, —CO—, —$CH_2$—, CH(OH), $SO_2$, SO, $CH_2$—O, or CONH; or a group $CF_2H$—A'— where A' is oxygen, sulphur, SO, $SO_2$, $CF_2$ or CFH; trifluoromethoxy, $C_{1-6}$ alkylsulphinyl, perfluoro $C_{2-6}$ alkylsulphonyl, $C_{1-6}$ alkylsulphonyl, $C_{1-6}$ alkoxysulphinyl, $C_{1-6}$ alkoxysulphonyl, aryl, heteroaryl, arylcarbonyl, heteroarylcarbonyl, phosphono, arylcarbonyloxy, heteroarylcarbonyloxy, arylsulphinyl, heteroarylsulphinyl, arylsulphonyl, or heteroarylsulphonyl in which any aromatic moiety is optionally substituted, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl, formyl, or amninosulphinyl, aminosulphonyl or aminocarbonyl, in which any amino moiety is optionally substituted by one or two $C_{1-6}$ alkyl groups, or $C_{1-6}$ alkylsulphinylamino, $C_{1-6}$ alkylsulphonylamino, $C_{1-6}$ alkoxysulphinylamino or $C_{1-6}$ alkoxysulphonylamino, or ethylenyl terminally substituted by $C_{1-6}$ alkylcarbonyl, nitro or cyano, or —C($C_{1-6}$ alkyl)NOH or —C($C_{1-6}$ alkyl)NNH$_2$; or amino optionally substituted by one or two $C_{1-6}$ alkyl or by $C_{2-7}$ alkanoyl; one of $R_3$ and $R_4$ is hydrogen or $C_{1-4}$ alkyl and the other is $C_{1-4}$ alkyl, $CF_3$ or $CH_2 X^a$ is fluoro, chloro, bromo, iodo, $C_{1-4}$ alkoxy, hydroxy, $C_{1-4}$ alkylcarbonyloxy, —S—$C_{1-4}$ alkyl, nitro, amino optionally substituted by one or two $C_{1-4}$ alkyl groups, cyano or $C_{1-4}$ alkoxycarbonyl; or $R_3$ and $R_4$ together are $C_{2-5}$ polymethylene optionally substituted by $C_{1-4}$ alkyl;

$R_5$ is $C_{1-6}$ alkylcarbonyloxy, benzoyloxy, $ONO_2$, benzyloxy, phenyloxy or $C_{1-6}$ alkoxy and $R_6$ and $R_9$ are hydrogen or $R_5$ is hydroxy and $R_6$ is hydrogen or $C_{1-2}$ alkyl and $R_9$ is hydrogen;

$R_7$ is heteroaryl or phenyl, both of which are optionally substituted one or more times independently with a group or atom selected from chloro, fluoro, bromo, iodo, nitro, amino optionally substituted once or twice by $C_{1-4}$ alkyl, cyano, azido, $C_{1-4}$ alkoxy, trifluoromethoxy and trifluoromethyl;

$R_8$ is hydrogen, $C_{1-6}$ alkyl, $OR_{11}$ or $NHCOR_{10}$ wherein $R_{11}$ is hydrogen, $C_{1-6}$ alkyl, formyl, $C_{1-6}$ alkanoyl, aroyl or aryl-$C_{1-6}$ alkyl and $R_{10}$ is hydrogen, $C_{1-6}$ alkyl, $C_{1-6}$ alkoxy, mono or di $C_{1-6}$ alkyl amino, amino, amino-$C_{1-6}$ alkyl, hydroxy-$C_{1-6}$ alkyl, halo-$C_{1-6}$ alkyl, $C_{1-6}$ acyloxy-$C_{1-6}$ alkyl, $C_{1-6}$ alkoxycarbonyl-$C_{1-6}$-alkyl, aryl or heteroaryl; the $R_8$—N—CO—$R_7$ group being cis to the $R_5$ group;

and X is oxygen or $NR_{12}$ where $R_{12}$ is hydrogen or $C_{1-6}$ alkyl.

2. The method according to claim 1 wherein, in the compound of formula (I), $R_2$ is hydrogen.

3. The method according to claim 1 wherein, in the compound of formula (I), $R_3$ and $R_4$ are both methyl.

4. The method according to claim 1 wherein, in the compound of formula (I), $R_5$ is hydroxy and $R_6$ and $R_9$ are hydrogen.

5. The method according to claim 1 wherein, in the compound of formula (I), $R_7$ is 2-, 3-, or 4-fluorophenyl, phenyl, 2 or 3-chlorophenyl, 2,3-dichlorophenyl, 2-trifluoromethylphenyl, 2-nitrophenyl, 2-aminophenyl, 2-chloro-thiophene-3-yl, 3-chlorothiophen-2-yl or 2-chloro-4-fluoro.

6. The method according to claim 1 wherein, in the compound of formula (I), $R_8$ is hydrogen.

7. The method according to claim 1 wherein the compound of formula (I) is selected from the list consisting of:

cis-(±)-6-Acetyl-4-(4-fluorobenzoylamino)-3,4-dihydro-2,2-dimethyl-2H-1-benzopyran-3-ol;

cis-6-Acetyl-4R-(4-fluorobenzoylamino)-3,4-dihydro-2,2-dimethyl-2H-1-benzopyran-3R-ol;

cis-6-Acetyl-4S-(4-fluorobenzoylamino)-3,4-dihydro-2,2-dimethyl-2H-1-benzopyran-3S-ol;

cis-6-Acetyl-4S-(2-chlorobenzoylamino)-3,4-dihydro-2,2-dimethyl-2H-1-benzopyran-3S-ol;

cis-6-Acetyl-4S-(benzoylamino)-3,4-dihydro-2,2-dimethyl-2H-1-benzopyran-3S-ol;

cis-6-Acetyl-4S-(2-methylbenzoylamino)-3,4-dihydro-2,2-dimethyl-2H-1-benzopyran-3S-ol;

cis-6-Acetyl-4-(2,3-dichlorobenzoylamino)-3,4-dihydro-2,2-dimethyl-2H-1-benzopyran-3-ol;

cis-6-Acetyl-4S-(2-trifluoromethylbenzoylamino)-3,4-dihydro-2,2-dimethyl-2H-1-benzopyran-3S-ol;

cis-6-Acetyl-4S-(2-fluorobenzoylamino)-3,4-dihydro-2,2-dimethyl-2H-1-benzopyran-3S-ol;

cis-6-Acetyl-4S-(3-fluorobenzoylamino)-3,4-dihydro-2,2-dimethyl-2H-1-benzopyran-3S-ol;

cis-6-Acetyl-4S-(2-nitrobenzoylamino)-3,4-dihydro-2,2-dimethyl-2H-1-benzopyran-3S-ol;

cis-6-Acetyl-4S-(2-aminobenzoylarnino)-3,4-dihydro-2,2-dimethyl-2H-1-benzopyran-3S-ol;

cis-6-Acetyl-4S-(3-chlorobenzoylamino)-3,4-dihydro-2,2-dimethyl-2H-1-benzopyran-3S-ol;

cis-6-Acetyl-4S-(2-chlorothiophen-3-carbonylamino)-3,4-dihydro-2,2-dimethyl-2H-1-benzopyran-3S-ol;

cis-6-Acetyl-4S-(2-chloro-4-fluorobenzoylamino)-3,4-dihydro-2,2-dimethyl-2H-1-benzopyran-3-ol.

8. The method according to claim 1 wherein the effects associated with withdrawal from substances of abuse are effects associated with withdrawal from substances selected from cocaine, nicotine, alcohol and benzodiazepines.

9. The method according to claim 1 wherein the disorder treatable with anti-convulsive agents is epilepsy.

* * * * *